United States Patent [19]

Lewis

[11] 4,305,930
[45] Dec. 15, 1981

[54] SYNERGISTIC DEODORANT COMPOSITIONS

[75] Inventor: Ronald G. Lewis, Phoenix, Ariz.

[73] Assignee: Armour-Dial, Inc., Phoenix, Ariz.

[21] Appl. No.: 95,311

[22] Filed: Nov. 19, 1979

Related U.S. Application Data

[63] Continuation of Ser. No. 843,904, Oct. 20, 1977, abandoned.

[51] Int. Cl.³ .................. A61K 7/32; A61K 7/36; A61K 9/12
[52] U.S. Cl. .................... 424/65; 252/106; 252/107; 424/DIG. 5; 424/46; 424/47; 424/67; 424/168
[58] Field of Search .............. 424/65, 47, 46, 168; 252/106, 107

[56] References Cited

U.S. PATENT DOCUMENTS 3,288,681 11/1966 Goldberg et al. .................. 424/47
3,493,650 2/1970 Dunkel .................. 424/65

FOREIGN PATENT DOCUMENTS 2351927 4/1975 Fed. Rep. of Germany ........ 424/65

OTHER PUBLICATIONS

La Parfumerie Moderne, Nov.-Dec. 1952, vol. 44:30, pp. 64 to 74.

*Primary Examiner*—Dale R. Ore
*Attorney, Agent, or Firm*—Frank T. Barber; Charles E. Cates; Richard G. Harrer

[57] ABSTRACT

The disclosure teaches a synergistic deodorant combination of citronellyl senecioate with 3-trifluoromethyl-4,4'-dichlorocarbanilide or 3,4,4'trichlorocarbanilide. The disclosure also teaches synergistic combinations of the foregoing ingredients with 2,4,4'-trichloro-2'-hydroxy diphenyl ether. The foregoing ingredients show synergistic activity as deodorants in various combinations and concentrations as set out in the disclosure. The structures of the ingredients are shown below.

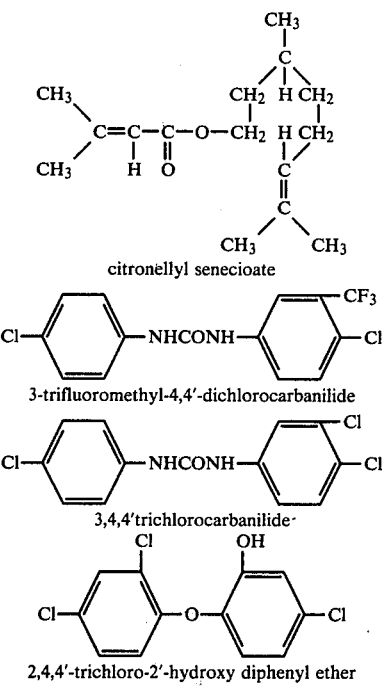

8 Claims, 4 Drawing Figures

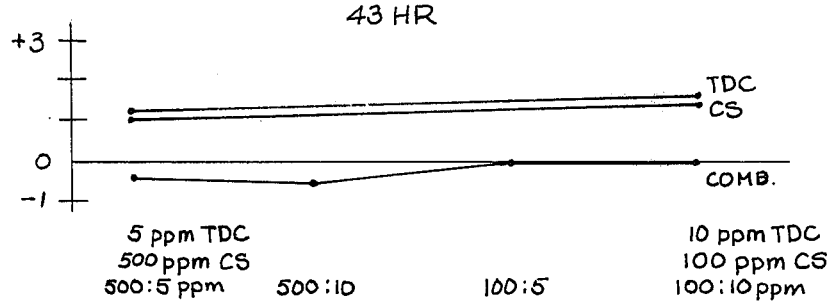
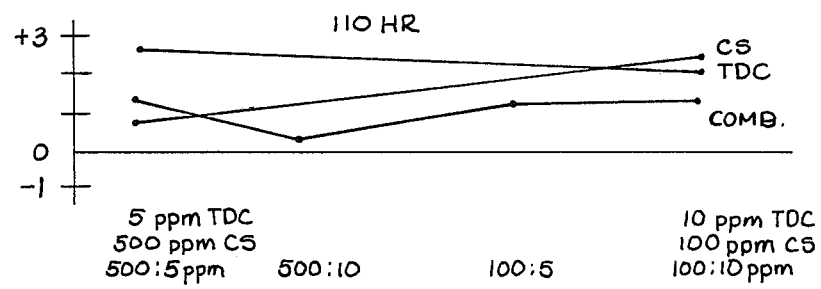
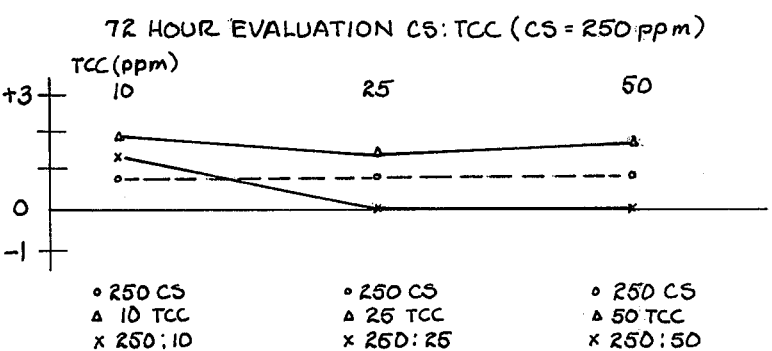
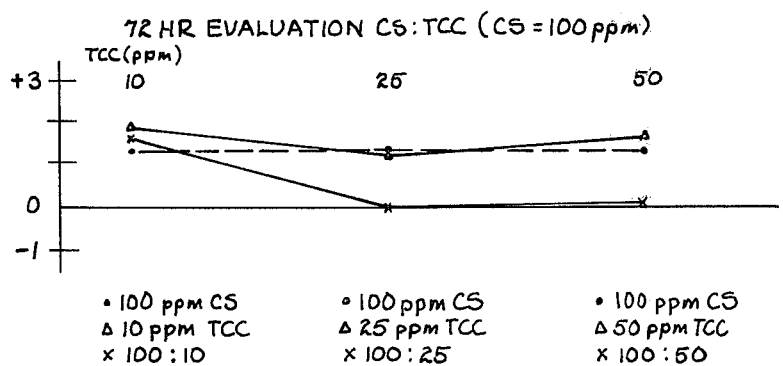
MAXIMUM ODOR SCORE = 3+

SYNERGISTIC DEODORANT COMPOSITIONS

This is a continuation of application Ser. No. 843,904, filed Oct. 20, 1977, now abandoned.

BACKGROUND OF THE INVENTION

This invention relates to the personal care field, particularly to preparations for use by humans as underarm deodorants.

Underarm deodorant preparations are convenient chemical aids to keeping the human body's odors unobtrusive and the owner socially acceptable. Deodorant ingredients that are safe and efficacious are known; however, they are expensive ingredients and a continuing need exists for less expensive active ingredients or ways of making existing ingredients go farther.

BRIEF SUMMARY OF THE INVENTION

From among the numerous deodorant substances known in the art, I have discovered that a combination of citronellyl senecioate (sometimes hereafter referred to as CS), having the structure:

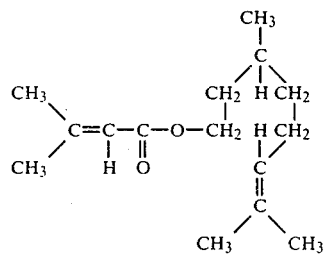

with carbanilides having the general structure:

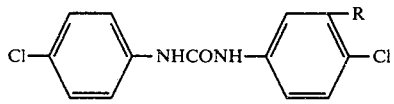

wherein R is selected from the group consisting of $CF_3$ and Cl, which are 3-trifluoromethyl-4, 4'-dichlorocarbanilide (sometimes hereafter referred to as TDC) and 3,4,4' trichlorocarbanilide (sometimes hereafter referred to as TCC) respectively, or mixtures of the two, yields an unexpected synergestic potentiation of the deodorant capabilities of the ingredients; and further, that a combination of citronellyl senecioate, 3,4,4' trichlorocarbanilide and/or 3-trifluoromethyl-4,4'-dichlorocarbanilide and a compound having the structure:

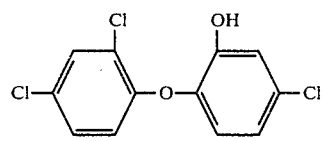

which is 2,4,4'-trichloro-2'-hydroxy diphenyl ether (sometimes hereinafter referred to as DPE) also has synergistic deodorant properties. Owing to the synergistically enhanced efficacy, less of the combined active ingredients is required to obtain the effect of a greater quantity of the prior art active ingredients used separately.

The synergistic results of this invention occur in such compositions containing the following concentrations: from about 25 to 500 parts per million of citronellyl senecioate, from about 10 to 500 parts per million of TCC or from about 0.1 to 10 parts per million of TDC. Any of the foregoing combinations with the addition of about 0.1 to 1 part per million DPE is also synergistic.

DETAILED DESCRIPTION OF PREFERRED EMBODIMENTS

The ingredients of the synergistic deodorant combination of this invention can be combined at ambient temperatures and atmospheric pressures by simple mixing.

The resulting composition can be incorporated into product formulations by state of the art methods known to those skilled in the art. The following are examples of products which can be made by incorporating the composition of this invention.

EXAMPLE I

Deodorant Cleansing Bar

Soap pellets are mixed with a synergistic combination of this invention according to the ranges in Schedule A below. Additional optional ingredients such as, without limitation: brighteners, dispersing agents, colors and preservatives, may be added as desired. The optional ingredients and TCC are mixed together in water and the resulting slurry is added to the soap pellets in the amalgamator. Then the CS and perfume are mixed together and added to the soap pellets. The ingredients are processed into finished soap bars in the usual manner of making soap bars.

| | Schedule A | | | | |
|---|---|---|---|---|---|
| | 85/15 tallow/coco 8% Moisture | Synthetic Detergent | TCC/CS 1:2 | % Water | % Optional | % Perfume |
| A. | 50 | 28.5 | 5.0 | 14 | 0.5 | 2.0 |
| B. | 90 | 0 | 0.5 | 8.9 | 0.1 | 0.5 |
| C. | 70 | 19.1 | 2.0 | 8.0 | 0.2 | 0.7 |
| D. | 70 | 19.3 | 1.0 | 8.0 | 0.2 | 1.5 |

EXAMPLE II

Stick Deodorant

Expressing parts by weight:

1st moiety: Mix 42 parts ethyl alcohol, 3 parts propylene glycol, 6 parts sodium stearate and 0.01 part TDC together and heat to 50° C. and until a clear solution is obtained.

2nd moiety: Add 0.5 parts CS to perfume q.s. and mix

Add the 2nd moiety to the 1st moiety at 50° C. and mix well. Let product cool to about 35° C. and place in container to cool to ambient temperature.

EXAMPLE III

Water-in-Oil Deodorant Cream

| A | Mineral Oil | 20.00 |
|---|---|---|
| | Petrolatum | 8.50 |
| | Ceresin Wax | 6.00 |
| | Lanolin | 4.50 |
| | ARLACEL 83 | 4.00 |
| B | Magnesium Sulfate | 0.15 |
| | Water | 21.85 |
| C | Zinc Oxide | 15.00 |
| | Zinc Stearate | 10.00 |
| D | CS/TCC/DPE (100:50:1) | 10.00 |

| | | |
|---|---|---|
| | -continued | |
| E | Perfume | q.s. |

Procedure: Heat (A) to 80° C. Add (B) to (A) with stirring and continue to stir until emulsion reaches 50° C. Add (C) slowly with stirring and cool slowly to 40° C., continuing to stir during the cooling process. Add TDC plus DPE slowly with stirring. Mix the perfume with CS to get a uniform mixture, and then add and perfume and CS mixture to the formulation with stirring.

EXAMPLE IV

Aerosol Deodorant Powder

| | Ingredients: | |
|---|---|---|
| A | Talc | 11.65 |
| | Zinc Oxide | 0.80 |
| | Magnesium Stearate | 1.20 |
| B | Isopropyl Myristate | 0.50 |
| | Sorbitan sesquioleate | 0.50 |
| | CS/TDC (50:1) | 0.25 |
| C | Freon 11 | 55.05 |
| | Freon 12 | 30.05 |
| D | Perfume | q.s. |

Mix ingredients of (A). Dissolve CS/TDC in warm isopropyl myristate; Cool and add Sorbitan sesquioleate, perfume. Then add (A) to (B) with constant stirring to form a slurry. Cold or pressure fill container with (C) using powder spray head.

EXAMPLE V

Deodorant Aerosol

Dissolve the following ingredients in alcohol:

| Concentrate: | | % in Aerosol 40.0 |
|---|---|---|
| 1. SDA 40 Anhydrous | 93.20 | |
| 2. Zinc Phenolsulfonate | 4.25 | |
| 3. CS/TDC (10:1) | 0.30 | |
| 4. Propylene Glycol USP | 2.00 | |
| 5. Perfume | 0.25 | |
| Propellent: | | 60.0 |
| Isotron 12 | 40.00 | |
| Isotron 114 | 60.00 | |

The compositions of this invention were tested for efficacy at various concentrations and ratios, and compared to the efficacies of the single ingredients at various concentrations, explanations and examples of which follow.

In Vitro Deodorant Test

The synergistic odor-inhibiting properties of this invention were evaluated by in vitro deodorant tests. The in vitro test method involves the preparation of odor generating medium which evolves a strong body type odor upon inoculation with appropriate bacteria followed by incubation at 37° C. for 72 hours or longer. An incubation time of at least forty hours is generally needed for detection of odor generation.

EXAMPLE VI

Following the protocol of the in vitro deodorant test, varying ratios of CS:TDC were incorporated into the sweat medium as a DMF solution or suspension before inoculation and incubation. After incubation for periods of 43 and 110 hours on the average, a comparison of the odor generated in the medium-plus-active material with the odor generated in the medium-without-active indicated effectiveness against "body type" odors of bacterial origin at 43 hours (average) and 110 hours (average). The results are tabulated in Table I below. In Table I a comparison of (a) and (b) to (c) for example indicates that a 50:1 ratio does reduce odor dramatically.

The relationships in Table I are illustrated in FIGS. 1 and 2 of the drawings.

TABLE I

| | Concentration | | Odor* | |
|---|---|---|---|---|
| | CS | TDC | 43 Hr. Avg. | 110 Hr. Avg. |
| (a) | 0 | 0 | +1.6 | +2.4 |
| (b) | 500 ppm | 0 | +1.0 | +1.0 |
| (c) | 0 | 10 ppm | +1.6 | +2.0 |
| (d) | 500 ppm | 10 ppm | −0.5** | +0.3 |
| (e) | 0 | 5 ppm | +1.1 | +2.7 |
| (f) | 500 ppm | 5 ppm | −0.3 | +1.3 |
| (g) | 100 ppm | 0 | +1.5 | +2.2 |
| (h) | 100 ppm | 10 ppm | +0 | +1.3 |
| (i) | 100 ppm | 5 ppm | +0 | +1.2 |

*The maximum odor possible is +3.0 on our scale.
**The negative scores mean that the sample containing test chemical but uninoculated had more odor than the corresponding samples that were inoculated.

EXAMPLE VII

The protocol of Example VI was followed (with the exception noted below) using compounds CS:TCC with the results shown in Table II. The relationships in Table II are illustrated in FIGS. 3 and 4 of the drawings.

TABLE II

| Concentration | | |
|---|---|---|
| CS | TCC | Odor Score* |
| 0 | 0 | 1.8 |
| 250 ppm | 0 | 0.8 |
| 100 ppm | 0 | 1.4 |
| 0 | 50 ppm | 1.6 |
| 250 ppm | 50 ppm | 0 |
| 100 ppm | 50 ppm | 0.1 |
| 0 | 25 ppm | 1.3 |
| 250 ppm | 25 ppm | 0 |
| 100 ppm | 25 ppm | 0 |
| 0 | 10 ppm | 1.9 |
| 250 ppm | 10 ppm | 1.4 |
| 100 ppm | 10 ppm | 1.6 |

*These values are for 72 hour evaluations. The maximum odor score possible (water plus medium only) is +3.0.
The tubes were innoculated with S. epidermidis (24 hour culture).

Ratios of the combination CS:TCC:DPE were tested in vitro and the results appear in the next example. The data from Table III therein indicate synergism in the combinations CS:TCC:DPE at the ratios 100:10:0.5; 50:10:0.5; 100:10:0.1; 100:25:0.5; 50:25:0.5; 100:25:1; and 50:25:1. The best ratios are at 100:10:0.5 and 50:10:0.5.

EXAMPLE VIII

The protocol of Example VI was followed (with the exception noted below) using compounds CS:TCC:DPE with the results shown in Table III.

TABLE III

| Concentration | | | |
|---|---|---|---|
| CS | TCC | DPE | Odor Score* |
| 0 | 0 | 0 | 2.1 |
| 100 ppm | 0 | 0 | 1.4 |
| 50 ppm | 0 | 0 | 1.2 |
| 0 | 25 | 1 | 0.8 |

TABLE III-continued

| Concentration | | | |
|---|---|---|---|
| CS | TCC | DPE | Odor Score* |
| 100 ppm | 25 | 1 | 0.2 |
| 50 ppm | 25 | 1 | 0.1 |
| 0 | 10 | 1 | 0.6 |
| 100 ppm | 10 | 1 | 0.3 |
| 50 ppm | 10 | 1 | 0.3 |
| 0 | 25 | 0.5 | 0.8 |
| 100 ppm | 25 | 0.5 | 0.1 |
| 50 ppm | 25 | 0.5 | 0.1 |
| 0 | 10 | 0.5 | 1.4 |
| 100 ppm | 10 | 0.5 | 0.2 |
| 50 ppm | 10 | 0.5 | 0.2 |
| 0 | 25 | 0.1 | 0.3 |
| 100 ppm | 25 | 0.1 | 0.2 |
| 0 | 10 | 0.1 | 0.6 |
| 100 ppm | 10 | 0.1 | 0 |
| 0 | 0 | 1 | 1.5 |
| 0 | 0 | 0.5 | 2.2 |
| 0 | 0 | 0.1 | 2.0 |
| 50 ppm | 0 | 1 | 0.7 |
| 50 ppm | 0 | 0.5 | 1.4 |
| 50 ppm | 0 | 0.1 | 0.7 |

*These values are for 72 hour evaluations. The maximum odor score possible (water plus medium only) is +3.0. The tubes were innoculated with *S. epidermidis* (24 hour culture).

EXAMPLE IX

An in vivo deodorancy test of the composition of this invention in a 10:1 ratio of CS:TDC was conducted according to the following:

This test panel is carried out over a three week period and requires only one panelist per deodorant candidate. The final odor reduction attributable to each deodorant material is obtained by averaging all 6 hour and/or 24 hour period odor reduction values. The actual calculations used are illustrated below. The results as shown below are given additional significance by comparing them with similar values obtained by treating both axillae with placebo only under the same protocol.

| Hours After Initial Treatment | 6 | 24 | 30 | 48 | 54 | 72 | 78 | 96 |
|---|---|---|---|---|---|---|---|---|
| Week One Scores[a] | 13-13 | 16-13 | 16-13 | 19-13 | 19-14 | 19-12 | 20-14 | 20-11 |
| Week Two Scores[a] | 13-13 | 20-14 | 18-13 | 22-13 | 20-14 | 22-13 | 21-14 | 20-12 |
| Total Scores | 26-26 | 36-27 | 34-26 | 41-26 | 39-28 | 41-25 | 41-28 | 40-23 |
| Reduction Ratio[b] | 0/26 | 9/36 | 8/34 | 15/41 | 11/39 | 16/41 | 13/41 | 17/40 |
| % Odor Reduction | 0% | 25% | 24% | 37% | 28% | 39% | 32% | 43% |

[a]These scores are the sum of all judges employed. They also represent untreated side - treated side scores respectively.
[b]This ratio is untreated score minus treated score divided by untreated score.

6 hour odor reduction = $\frac{\text{6 hour period \% reductions}}{\text{number of 6 hour periods}} = \frac{84}{4} = 21\%$ 24 hour odor reduction = $\frac{\text{24 hour period \% reduction}}{\text{number of 24 hour periods}} = \frac{144}{4} = 36\%$ Over a two week active test period the CS:TDC combination effected a consistent and definite reduction in body odor.

The results of the test conducted are set forth below as Table IV.

TABLE IV

| Time after first active application | CS + TDC % Odor Reduction (a) | Placebo treatment of both axillae % Odor Reduction |
|---|---|---|
| 0 hr. | — | — |
| * 6 hr. | −5% (b) | +12% |
| ** 24 hr. | −1% | −20% |
| * 30 hr. | +12% | +10% |
| ** 48 hr. | +20% | −8% |
| * 54 hr. | +18% | −7% |
| ** 72 hr. | +24% | −13% |
| * 78 hr. | +15% | −12% |
| ** 96 hr. | — (c) | +7% |

(a) This ratio is untreated score minus treated score divided by untreated score.
(b) A negative value indicates that the treated axilla had a higher odor than the untreated axilla.
(c) No value was taken for this time period.

| | | |
|---|---|---|
| * 6 hour odor Reduction Average | +10% | +1% |
| ** 24 hour odor Reduction Average | +14% | −9% |

What is claimed is:

1. A composition of matter comprising the synergistic, deodorant combination, by weight, of about 100 to 250 parts citronellyl senecioate and about 25 to 50 parts 3,4,4' trichlorocarbanilide.

2. The composition of claim 1 wherein citronellyl senecioate comprises about 250 parts and 3,4,4' trichlorocarbanilide comprises about 50 parts.

3. The composition of claim 1 wherein citronellyl senecioate comprises about 100 parts and 3,4,4' trichlorocarbanilide comprises about 50 parts.

4. The composition of claim 1 wherein citronellyl senecioate comprises about 100 parts and 3,4,4' trichlorocarbanilide comprises about 25 parts.

5. A composition of matter comprising the synergistic, deodorant combination, by weight, of about 100 to 500 parts citronellyl senecioate and about 5 to 10 parts 3-trifluoromethyl-4, 4'-dichlorocarbanilide.

6. The composition of claim 5 wherein citronellyl senecioate comprises about 500 parts and 3-trifluoromethyl-4, 4'-dichlorocarbanilide comprises about 10 parts.

7. The composition of claim 5 wherein citronellyl senecioate comprises about 100 parts and 3-trifluoromethyl-4, 4'-dichlorocarbanilide comprises about 10 parts.

8. The composition of claim 5 wherein citronellyl senecioate comprises about 100 parts and 3-trifluoromethyl-4, 4'-dichlorocarbanilide comprises about 5 parts.

* * * * *